(12) United States Patent
Kobayashi

(10) Patent No.: US 11,615,270 B2
(45) Date of Patent: Mar. 28, 2023

(54) MEDICAL IMAGE PROCESSING APPARATUS, LEARNING METHOD, X-RAY DIAGNOSTIC APPARATUS, AND MEDICAL IMAGE PROCESSING METHOD

(71) Applicant: CANON MEDICAL SYSTEMS CORPORATION, Otawara (JP)

(72) Inventor: Yoshimasa Kobayashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 244 days.

(21) Appl. No.: 16/809,673

(22) Filed: Mar. 5, 2020

(65) Prior Publication Data

US 2020/0285902 A1    Sep. 10, 2020

(30) Foreign Application Priority Data

Mar. 6, 2019  (JP) .............................. JP2019-040876

(51) Int. Cl.
*G06K 9/62* (2022.01)
*G06T 11/00* (2006.01)
*A61B 6/00* (2006.01)
*A61B 6/02* (2006.01)

(52) U.S. Cl.
CPC ............ *G06K 9/6257* (2013.01); *A61B 6/025* (2013.01); *A61B 6/502* (2013.01); *A61B 6/5223* (2013.01); *G06T 11/008* (2013.01); *G06T 2210/41* (2013.01)

(58) Field of Classification Search
CPC ....... A61B 6/502; A61B 6/025; A61B 6/5223; G06V 10/82; G06V 2201/03; G06K 9/6257; G06K 9/6273; G06K 9/0057; G06K 9/6256; G06T 11/008; G06T 11/005; G06T 2211/436; G06T 2210/41
See application file for complete search history.

(56) References Cited

U.S. PATENT DOCUMENTS

| | | | |
|---|---|---|---|
| 9,792,703 B2 | 10/2017 | Costa et al. | |
| 10,679,384 B2* | 6/2020 | Palma | ........................ G06T 7/33 |
| 2017/0071562 A1* | 3/2017 | Suzuki | ................ A61B 6/5205 |
| 2019/0102916 A1* | 4/2019 | Palma | ...................... G06N 3/04 |
| 2019/0171914 A1* | 6/2019 | Zlotnick | ................ G16H 30/20 |

(Continued)

FOREIGN PATENT DOCUMENTS

| | | |
|---|---|---|
| JP | 2012-512669 | 6/2012 |
| WO | WO 2018/048507 A1 | 3/2018 |

OTHER PUBLICATIONS

Office Action dated Jan. 17, 2023 in Japanese Application No. 2019-040876.

*Primary Examiner* — Brenda C Bernardi
(74) *Attorney, Agent, or Firm* — Oblon, McClelland, Maier & Neustadt, L.L.P.

(57) ABSTRACT

A medical image processing apparatus of an embodiment includes processing circuitry. The processing circuitry is configured to acquire medical image data on the basis of tomosynthesis imaging of a test object, and input the acquired medical image data of the test object to a trained model to acquire a two-dimensional image data, the trained model being generated by learning of two-dimensional image data on the basis of X-ray imaging of a person and image data on the basis of tomosynthesis imaging of the person who is subjected to the X-ray imaging.

7 Claims, 14 Drawing Sheets

(56) References Cited

U.S. PATENT DOCUMENTS

2020/0085393 A1* 3/2020 Zhang ..................... A61B 6/54
2020/0202587 A1* 6/2020 Palma .................. G06T 11/006
2020/0211240 A1* 7/2020 Bernard ............... G06T 11/008
2021/0192810 A1* 6/2021 Paysan .................... G06N 3/08

* cited by examiner

MEDICAL IMAGE PROCESSING APPARATUS, LEARNING METHOD, X-RAY DIAGNOSTIC APPARATUS, AND MEDICAL IMAGE PROCESSING METHOD

CROSS-REFERENCE TO RELATED APPLICATION

The present application claims priority based on Japanese Patent Application No. 2019-040876, filed on Mar. 6, 2019, the content of which is incorporated herein by reference.

FIELD

Embodiments described herein and in figures relate to a medical image processing apparatus, a learning method, an X-ray diagnostic apparatus, and a medical image processing method.

BACKGROUND

Tomosynthesis imaging for sequentially obtaining a plurality of pieces of projection data by radiating X-rays to a test object at a plurality of angles has been known. According to volume data obtained by reconstructing the plurality of pieces of projection data acquired through tomosynthesis imaging, a plurality of tomographic images (slice images) in a direction perpendicular to a reference direction (e.g., a normal direction of an imaging stand) is obtained. In the case of tomosynthesis imaging of a breast, tomographic images in which mammary glands rarely overlap are obtained, and thus clinical usefulness is provided for the high-density mammary gland which is difficult to delineate through mammography imaging.

A technology for generating a single two-dimensional image (composite 2D image) from a plurality of tomographic images acquired through tomosynthesis imaging has been known. For example, a technology called minimum intensity projection (MinIP) by which a two-dimensional image is generated by projecting, to pixels arranged in a slice direction of a plurality of tomographic images, a minimum value in a pixel group arranged in a direction perpendicular to the slice direction has been known. According to a two-dimensional image generated according to this type of technology, a plurality of tomographic images obtained through tomosynthesis imaging can be provided as a single digest image.

However, in the case of a two-dimensional image (composite 2D image) generated by the aforementioned technology, with respect to pixels arranged in a slice direction of a plurality of tomographic images, only a single pixel value (a minimum value in the case of MinIP) in a pixel group arranged in a direction perpendicular to the slice direction is reflected and other pixel values are not reflected. Accordingly, information on the mammary gland that is a background of calcification, and the like, for example, are not included therein. In addition, X-rays radiated in tomosynthesis imaging are lower than X-rays radiated in mammography imaging. Accordingly, two-dimensional images generated by the aforementioned technology have contrast considerably different from that of images obtained through mammography imaging. Furthermore, since X-rays are radiated while moving an X-ray tube in tomosynthesis imaging, tomographic images obtained through tomosynthesis imaging include artifacts associated with movement of the X-ray tube. This also affects two-dimensional images generated by the aforementioned technology.

DETAILED DESCRIPTION

A medical image processing apparatus of an embodiment includes processing circuitry. The processing circuitry is configured to acquire medical image data on the basis of tomosynthesis imaging of a test object, and input the acquired medical image data of the test object to a trained model to acquire a two-dimensional image data, the trained model being generated by learning of two-dimensional image data on the basis of X-ray imaging of a person and image data on the basis of tomosynthesis imaging of the person who is subjected to the X-ray imaging.

Hereinafter, a medical image processing apparatus, a learning method, an X-ray diagnostic apparatus, and a medical image processing method of embodiments will be described with reference to the drawings.

First Embodiment

Figure 1:
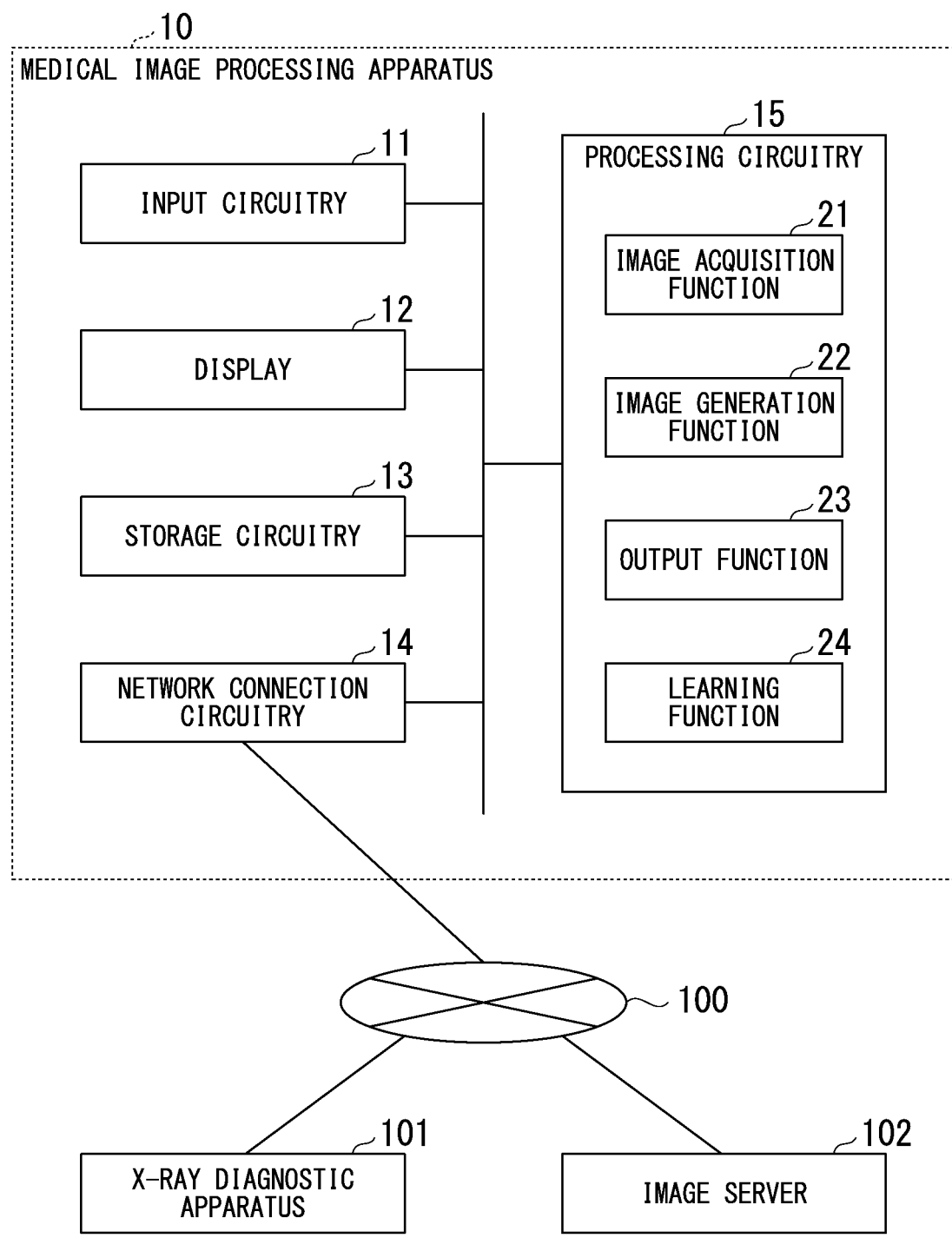
FIG. 1 is a block diagram showing an example of a configuration of a medical image processing apparatus 10 according to a first embodiment.

FIG. 1 is a block diagram showing an example of a configuration of a medical image processing apparatus 10 according to a first embodiment. The medical image processing apparatus 10 includes input circuitry 11, a display 12, storage circuitry 13, network connection circuitry 14, and processing circuitry 15.

The input circuitry 11 includes a general input device such as a trackball, a switch button, a mouse, a keyboard, or a numeric keypad, for example, and outputs an operation input signal in accordance with an operation of a user to the processing circuitry 15. The display 12 includes a general display output device such as a liquid crystal display, or an organic light emitting diode (OLED) display, for example.

The storage circuitry 13 has a configuration including a processor-readable recording medium such as a semiconductor device such as a random access memory (RAM) or a flash memory, a hard disk, or an optical disc, for example, and stores programs and parameters used by the processing circuitry 15 and other types of data. Some or all of programs and data in the recording medium of the storage circuitry 13 may be downloaded through communication through a network 100 or provided to the storage circuitry 13 through a portable storage medium such as an optical disc.

In addition, the storage circuitry 13 may store projection data based on tomosynthesis imaging of a test object acquired through the network 100 or volume data reconstructed on the basis of the projection data.

The network connection circuitry 14 implements various information communication protocols according to the type of the network 100. The network connection circuitry 14 connects to other electronic apparatuses through the network 100 according to the various protocols. The network 100 is a general information communication network using a telecommunications technology, and examples of which include a telephone communication line network, an optical fiber communication network, a cable communication network, a satellite communication network, etc. in addition to wireless/wired LANs such as a hospital based local area network (LAN) and the Internet.

The medical image processing apparatus 10 is connected to an X-ray diagnostic apparatus 101 and an image server 102 through the network 100 such that they can transmit/receive data to/from each other.

The X-ray diagnostic apparatus 101 includes, for example, a mammography apparatus which performs tomosynthesis imaging or mammography imaging of a breast, an X-ray TV apparatus which performs long tomosynthesis imaging, and the like.

The processing circuitry 15 realizes a function of integrally controlling the medical image processing apparatus 10. The processing circuitry 15 is a processor which reads and executes a program stored in the storage circuitry 13. The processing circuitry 15 generates two-dimensional image data on the basis of medical image data associated with tomosynthesis imaging. Specifically, the medical image data associated with tomosynthesis imaging is projection data acquired through tomosynthesis imaging or volume data reconstructed from the projection data.

As shown in FIG. 1, the processing circuitry 15 realizes an image acquisition function 21, an image generation function 22, an output function 23, and a learning function 24. These functions are stored in the form of programs in the storage circuitry 13. The image acquisition function 21 and the image generation function 22 functions after a trained model 32 is generated and the output function 23 and the learning function 24 functions to generate the trained model 32.

The image acquisition function 21 acquires medical image data associated with tomosynthesis imaging of a test object from the X-ray diagnostic apparatus 101 or the image server 102 as first medical image data. The image acquisition function 21 is an example of an image acquirer.

The image generation function 22 generates two-dimensional image data of the test object on the basis of the first medical image data acquired by the image acquisition function 21 as second medical image data. The image generation function 22 uses a trained model (the trained model 32 which will be described later) which outputs the second medical image data by receiving the first medical image data. The image generation function 22 generates the two-dimensional image data of the test object by inputting the medical image data (first medical image data) associated with tomosynthesis imaging of the test object to the trained model. The image generation function 22 is an example of an image generator.

The output function 23 outputs the medical image data (first medical image data) associated with tomosynthesis imaging of the test object performed in the X-ray diagnostic apparatus 101 and the medical image data (second medical image data) that is two-dimensional image data associated with X-ray imaging of the same test object as a data set for learning.

For example, mammography imaging of a breast is performed with a larger dose of X-rays than that radiated in tomosynthesis imaging of a breast. When tomosynthesis imaging of a breast is performed, mammography imaging of the breast is generally also performed. Accordingly, the first medical image data and the second medical image data acquired through a conventional workflow can be used as a data set for learning to improve the efficiency. The output function 23 is an example of an output unit.

Figure 2:
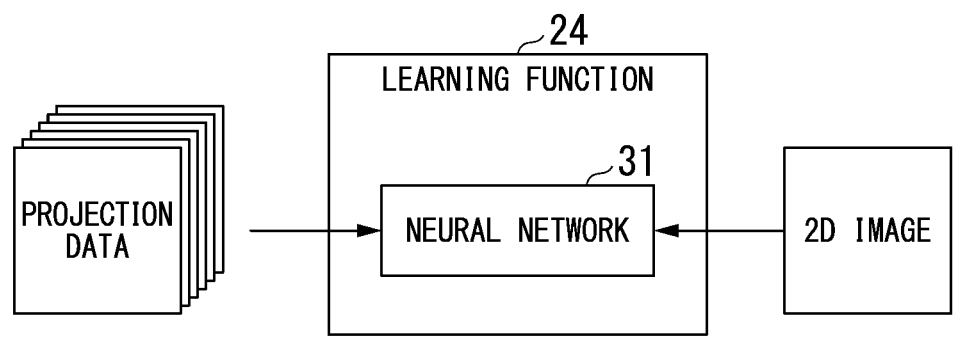
FIG. 2 is a diagram showing an example of a data flow during learning of a learning function 24 according to the first embodiment.

The learning function 24 performs deep learning on the basis of the data set for learning output from the output function 23. As shown in FIG. 2, the learning function 24 uses a plurality of pieces of projection data (the first medical image data) associated with tomosynthesis imaging of the test object as training input data. The learning function 24 uses two-dimensional image data (the second medical image data) associated with X-ray imaging of the same test object as training output data.

Figure 3:
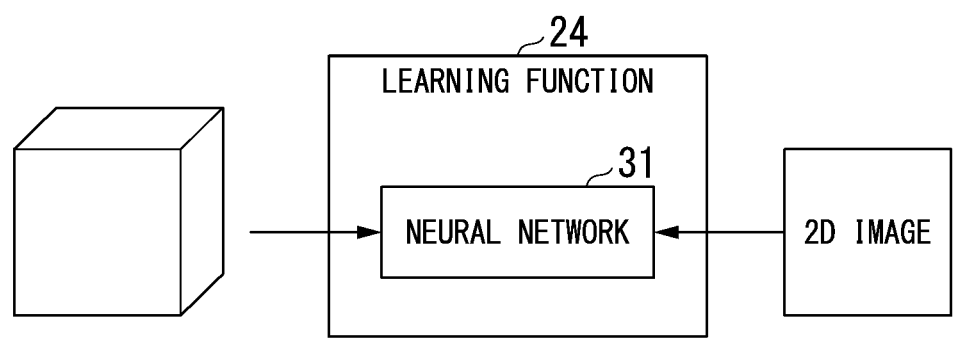
FIG. 3 is a diagram showing another example of a data flow during learning of the learning function 24 according to the first embodiment.

The first medical image data used as the training input data may be volume data reconstructed from projection data instead of the projection data acquired through tomosynthesis imaging. That is, the learning function 24 may use the volume data (first medical image data) reconstructed from a plurality of pieces of projection data of the test object as the training input data, as shown in FIG. 3. Further, the first medical image data used as the training input data may be a combination of the projection data acquired through tomosynthesis imaging and the volume data reconstructed from the projection data.

The learning function 24 performs update of parameter data of a neural network 31 such that a result of processing of training input data (medical image data associated with tomosynthesis imaging of the test object) in the neural network 31 approaches training output data (two-dimensional image data associated with X-ray imaging of the same test object), known as learning, whenever a data set for learning is input. The parameter data of the neural network 31 is adjusted and updated through a method such as back propagation of a convolution neural network (CNN), for example. The learning function 24 determines that learning ends when a change rate of the parameter data converges within a threshold value. The learning function 24 generates the trained model 32 having a form of a deep neural network (DNN), for example, on the basis of the parameter data after learning. The trained model 32 is stored in the storage circuitry 13 and read from the storage circuitry 13 during operation. Further, the trained model 32 may be constructed using an integrated circuit such as an application specific integrated circuit (ASIC) or a field programmable gate array (FPGA).

Figure 4:
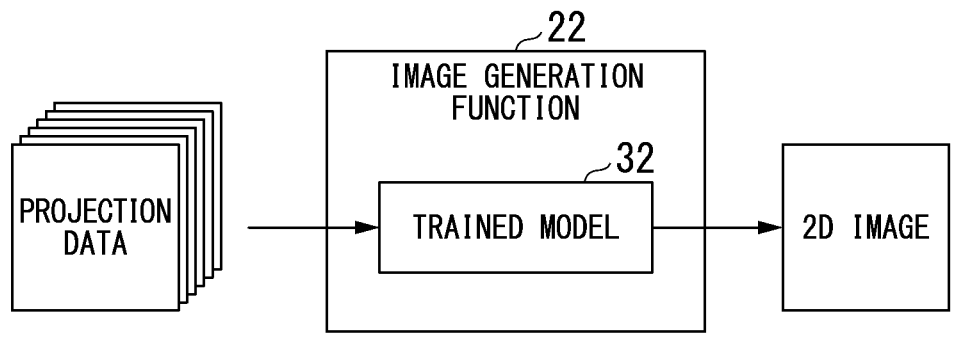
FIG. 4 is a diagram showing an example of a data flow during operation of an image generation function 22 according to the first embodiment.
Figure 5:
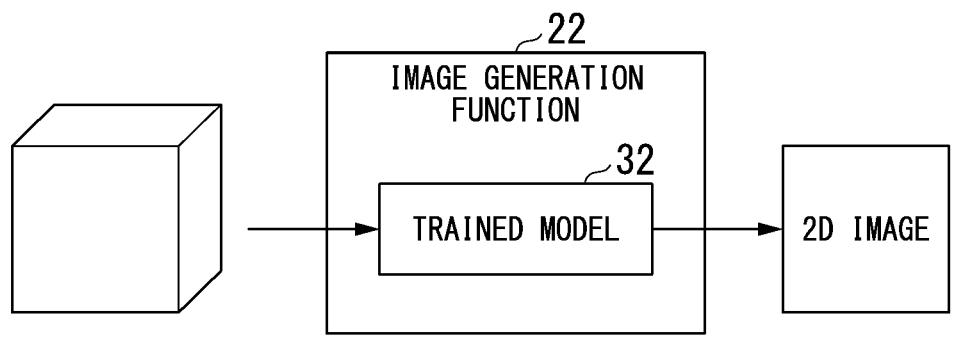
FIG. 5 is a diagram showing another example of a data flow during operation of the image generation function 22 according to the first embodiment.

The type of training input data and the type of input data during operation shown in FIG. 4 and FIG. 5 need to be consistent with each other. For example, an angle range and an angle graduation (e.g., a total of 16 angles including −7.5° to +7.5° with a graduation of 1°) of a projection data group as training input data during learning need to be consistent with an angle range and angle graduation of input data during operation.

The operation of the medical image processing apparatus 10 configured as above during operation will be described below.

The image acquisition function 21 acquires medical image data associated with tomosynthesis imaging of the test object from the X-ray diagnostic apparatus 101 or the image server 102 as the first medical image data. The image generation function 22 generates two-dimensional image data of the test object as the second medical image data on the basis of the first medical image data acquired by the image acquisition function 21.

For example, the image generation function 22 may generate the two-dimensional image data of the test object by inputting a plurality of pieces of projection data (the first medical image data) associated with tomosynthesis imaging of the test object to the trained model 32, as shown in FIG. 4. Further, the image generation function 22 may generate the two-dimensional image data of the test object by inputting volume data (the first medical image data) reconstructed from the plurality of pieces of projection data of the test object to the trained model 32, as shown in FIG. 5.

Since the two-dimensional image data generated by the image generation function 22 corresponds to X-ray imaging of a two-dimensional image such as mammography imaging, the contrast of the two-dimensional image data is the same as that of an image acquired through mammography imaging in reality. In addition, the two-dimensional image data generated by the image generation function 22 has a large amount of information arranged in a direction perpendicular to the slice direction, and information on the mammary gland that is a background of calcification, and the like can be confirmed, for example, as compared to a two-dimensional image (composite 2D image) generated through a technology such as MinIP. Further, the two-dimensional image data generated by the image generation function 22 is not also affected by artifacts associated with movement of an X-ray tube in tomosynthesis imaging.

According to the first embodiment described above, since the image acquisition function 21 which acquires medical image data associated with tomosynthesis imaging of a test object as the first medical image data and the image generation function 22 which generates the second medical image data of the same test object by inputting the first medical image data to the trained model 32 which generates the second medical image data that is two-dimensional image data associated with X-ray imaging on the basis of the first medical image data are provided, it is possible to obtain a high-definition two-dimensional image from images associated with tomosynthesis imaging.

Second Embodiment

Hereinafter, a second embodiment will be described. The second embodiment differs from the first embodiment with respect to details of the first medical image data.

The output function 23 in the second embodiment outputs, as a data set for learning, medical image data associated with tomosynthesis imaging of a test object which is performed in the X-ray diagnostic apparatus 101, more specifically, some projection data (first medical image data) in which angles associated with two-dimensional image data are about 0° from among a plurality of pieces of projection data acquired through tomosynthesis imaging, and medical image data (second medical image data) that is two-dimensional image data associated with X-ray imaging of the same test object. The output function 23 may output, as the first medical image data, some tomographic image data in which angles associated with the two-dimensional image data are about 0°, which is extracted from volume data reconstructed from the plurality of pieces of projection data acquired through tomosynthesis imaging of the test object.

Figure 6:
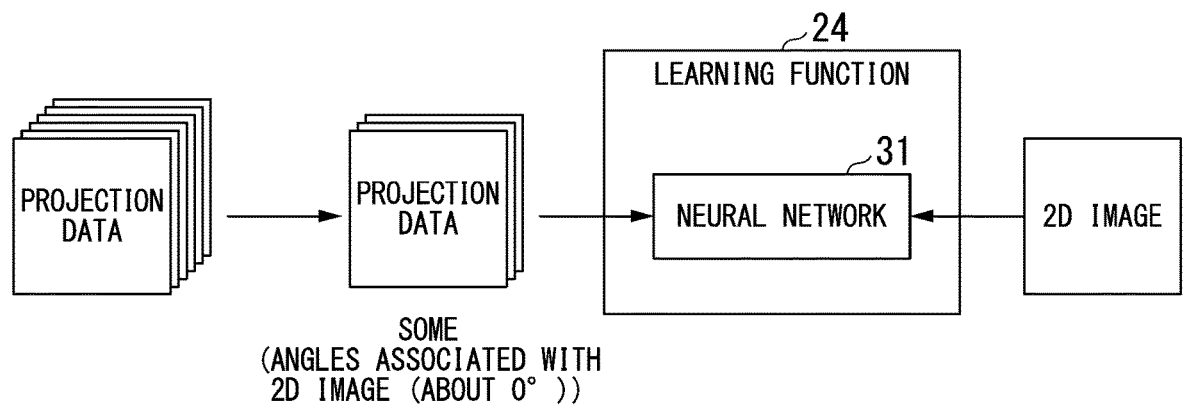
FIG. 6 is a diagram showing an example of a data flow during learning of a learning function 24 according to a second embodiment.

The learning function 24 performs deep learning on the basis of the data set for learning output from the output function 23. As shown in FIG. 6, the learning function 24 uses, as training input data, some projection data (first medical image data) in which angles associated with the two-dimensional image data are about 0° from among the plurality of pieces of projection data acquired through tomosynthesis imaging of the test object. In addition, the learning function 24 uses, as training output data, the two-dimensional image data (second medical image data) associated with X-ray imaging of the same test object. Further, the learning function 24 may use, as the training input data, some tomographic image data (first medical image data) in which angles associated with the two-dimensional image data are about 0°, which is extracted from the volume data reconstructed from the plurality of pieces of projection data acquired through tomosynthesis imaging of the test object.

The learning function 24 performs update of parameter data of the neural network 31 such that a result of processing of the training input data (some projection data in which angles associated with two-dimensional image data are about 0° from among a plurality of pieces of projection data acquired through tomosynthesis imaging of the test object) in the neural network 31 approaches the training output data (two-dimensional image data associated with X-ray imaging of the same test object), known as learning, whenever a data set for learning is input. The parameter data of the neural network 31 is adjusted and updated through a method such as back propagation of a CNN, for example. The learning function 24 determines that learning ends when a change rate of the parameter data converges within a threshold value. The learning function 24 generates the trained model 32 having a form of a DNN, for example, on the basis of the parameter data after learning. The trained model 32 is stored in the storage circuitry 13 and read from the storage circuitry 13 during operation. Further, the trained model 32 may be constructed using an integrated circuit such as an ASIC or an FPGA.

Figure 7:
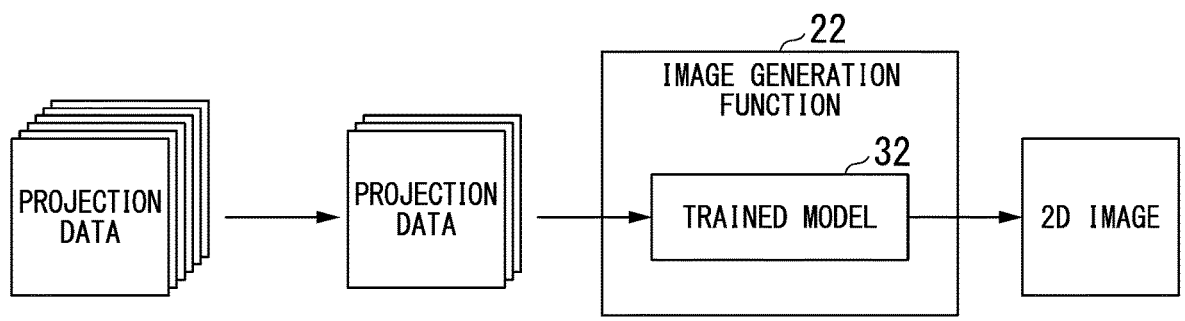
FIG. 7 is a diagram showing an example of a data flow during operation of an image generation function 22 according to the second embodiment.

The type of training input data and the type of input data during operation shown in FIG. 7 need to be consistent with each other. For example, angles (e.g., −1.5°, −0.5°, +0.5°, +1.5°, etc.) in some projection data or tomographic image data as training input data during learning need to be consistent with angles of input data during operation. The operation of the medical image processing apparatus 10 configured as above during operation will be described below.

The image acquisition function 21 acquires some projection data in which angles associated with two-dimensional image data are about 0° from among a plurality of pieces of projection data acquired through tomosynthesis imaging of a test object from the X-ray diagnostic apparatus 101 or the image server 102 as the first medical image data. The image generation function 22 generates two-dimensional image data of the test object as the second medical image data on the basis of the first medical image data acquired by the image acquisition function 21. Further, the image acquisition function 21 may acquire some tomographic image data in which angles associated with two-dimensional image data are about 0°, which is extracted from volume data reconstructed from the plurality of pieces of projection data acquired through tomosynthesis imaging of the test object, from the X-ray diagnostic apparatus 101 or the image server 102 as the first medical image data.

For example, the image generation function 22 generates the two-dimensional image data of the test object by inputting some projection data (first medical image data) in which angles associated with the two-dimensional image data are about 0° from among the plurality of pieces of projection data acquired through tomosynthesis imaging of the test object to the trained model 32, as shown in FIG. 7. Further, the image generation function 22 may generate the two-dimensional image data of the test object by inputting some tomographic image data (first medical image data) in which angles associated with the two-dimensional image data are about 0°, which is extracted from volume data reconstructed from the plurality of pieces of projection data acquired through tomosynthesis imaging of the test object to the trained model 32.

Since the two-dimensional image data generated by the image generation function 22 corresponds to X-ray imaging of a two-dimensional image such as mammography imaging, the contrast of the two-dimensional image data is the same as that of an image acquired through mammography imaging in reality. In addition, the two-dimensional image data generated by the image generation function 22 has a large amount of information arranged in a direction perpendicular to the slice direction, and information on the mammary gland that is a background of calcification, and the like can be confirmed, for example, as compared to a two-dimensional image (composite 2D image) generated through a technology such as MinIP. Further, the two-dimensional image data generated by the image generation function 22 is not affected by artifacts associated with movement of an X-ray tube in tomosynthesis imaging.

According to the second embodiment described above, since the image acquisition function 21 which acquires some projection data in which angles associated with two-dimensional image data are about 0° from among a plurality of pieces of projection data acquired through tomosynthesis imaging of a test object as the first medical image data and the image generation function 22 which generates the second medical image data of the same test object by inputting the first medical image data to the trained model 32 which generates the second medical image data that is two-dimensional image data associated with X-ray imaging on the basis of the first medical image data are provided, it is possible to obtain a high-definition two-dimensional image from images associated with tomosynthesis imaging.

Furthermore, according to the second embodiment, since the image acquisition function 21 which acquires some tomographic image data in which angles associated with two-dimensional image data are about 0° from among tomographic images of volume data reconstructed from a plurality of pieces of projection data acquired through tomosynthesis imaging of a test object as the first medical image data and the image generation function 22 which generates the second medical image data of the same test object by inputting the first medical image data to the trained model 32 which generates the second medical image data that is two-dimensional image data associated with X-ray imaging on the basis of the first medical image data are provided, it is possible to obtain a high-definition two-dimensional image from images associated with tomosynthesis imaging.

Third Embodiment

Hereinafter, a third embodiment will be described. The third embodiment differs from the first or second embodiment with respect to details of the first medical image data.

The output function 23 in the third embodiment outputs, as a data set for learning, medical image data associated with tomosynthesis imaging of a test object which is performed in the X-ray diagnostic apparatus 101, some projection data (first medical image data) in which angles associated with two-dimensional image data are about 0° from among a plurality of pieces of projection data acquired through tomosynthesis imaging, and medical image data (second medical image data) that is two-dimensional image data associated with X-ray imaging of the same test object. The output function 23 may output, as the first medical image data, the medical image data associated with tomosynthesis imaging of the test object, and some tomographic image data in which angles associated with the two-dimensional image data are about 0°, which is extracted from volume data reconstructed from the plurality of pieces of projection data acquired through tomosynthesis imaging of the test object.

Figure 8:
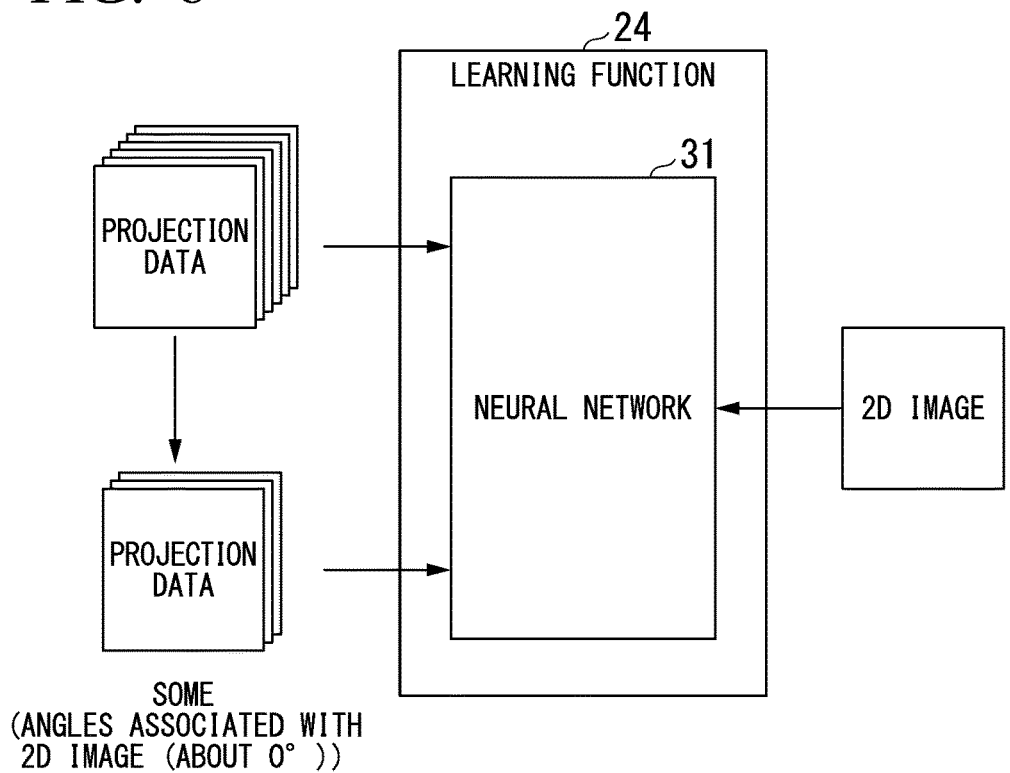
FIG. 8 is a diagram showing an example of a data flow during learning of a learning function 24 according to a third embodiment.

The learning function 24 performs deep learning on the basis of the data set for learning output from the output function 23. As shown in FIG. 8, the learning function 24 uses, as training input data, a plurality of pieces of projection data acquired through tomosynthesis imaging of the test object, and some projection data in which angles associated with the two-dimensional image data are about 0° from among the plurality of pieces of projection data as the first medical image data. The learning function 24 uses, as training output data, the two-dimensional image data (second medical image data) associated with X-ray imaging of the same test object. Further, the learning function 24 may use, as the training input data, volume data reconstructed from the plurality of pieces of projection data and some tomographic image data in which angles associated with the two-dimensional image data are about 0°, which is extracted from the volume data as the first medical image data.

The learning function 24 performs update of parameter data of the neural network 31 such that a result of processing of the training input data (medical image data associated with tomosynthesis imaging of the test object and some projection data in which angles associated with two-dimensional image data are about 0° from among a plurality of pieces of projection data acquired through tomosynthesis imaging) in the neural network 31 approaches the training output data (two-dimensional image data associated with X-ray imaging of the same test object), known as learning, whenever a data set for learning is input. The parameter data of the neural network 31 is adjusted and updated through a method such as back propagation of a CNN, for example. The learning function 24 determines that learning ends when a change rate of the parameter data converges within a threshold value. The learning function 24 generates the trained model 32 having a form of a DNN, for example, on the basis of the parameter data after learning. The trained model 32 is stored in the storage circuitry 13 and read from the storage circuitry 13 during operation. Further, the trained model 32 may be constructed using an integrated circuit such as an ASIC or an FPGA.

Figure 9:
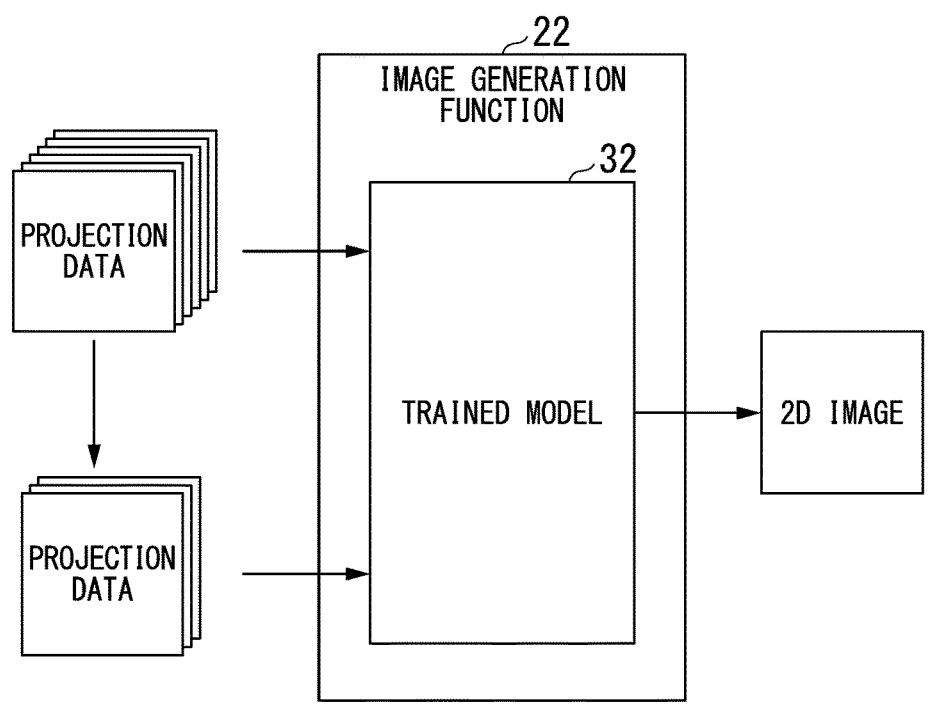
FIG. 9 is a diagram showing an example of a data flow during operation of an image generation function 22 according to the third embodiment.

In addition, the type of training input data and the type of input data during operation shown in FIG. 9 need to be consistent with each other. For example, angles (e.g., −1.5°, −0.5°, +0.5°, +1.5°, etc.) in some projection data or tomographic image data as training input data during learning need to be consistent with angles of input data during operation.

The operation of the medical image processing apparatus 10 configured as above during operation will be described below.

The image acquisition function 21 acquires a plurality of pieces of projection data acquired through tomosynthesis imaging of the test object and some projection data in which angles associated with two-dimensional image data are about 0° from among the plurality of pieces of projection data from the X-ray diagnostic apparatus 101 or the image server 102 as the first medical image data. The image generation function 22 generates two-dimensional image data of the test object as the second medical image data on the basis of the first medical image data acquired by the image acquisition function 21. Further, the image acquisition function 21 may acquire volume data reconstructed from the plurality of pieces of projection data acquired through tomosynthesis imaging of the test object and some tomographic image data in which angles associated with two-dimensional image data are about 0°, which is extracted from volume data, from the X-ray diagnostic apparatus 101 or the image server 102 as the first medical image data.

For example, the image generation function 22 may generate the two-dimensional image data of the test object by inputting a plurality of pieces of projection data acquired through tomosynthesis imaging of the test object and some projection data (first medical image data) in which angles associated with two-dimensional image data are about 0° from among the plurality of pieces of projection data to the trained model 32, as shown in FIG. 9. Further, the image generation function 22 may generate the two-dimensional image data of the test object by inputting volume data reconstructed from the plurality of pieces of projection data acquired through tomosynthesis imaging of the test object and some tomographic image data (first medical image data) in which angles associated with two-dimensional image data are about 0°, which is extracted from volume data, to the trained model 32.

Since the two-dimensional image data generated by the image generation function 22 corresponds to X-ray imaging of a two-dimensional image such as mammography imaging, the contrast of the two-dimensional image data is the same as that of an image acquired through mammography imaging in reality. In addition, the two-dimensional image data generated by the image generation function 22 has a large amount of information arranged in a direction perpendicular to the slice direction, and information on the mammary gland that is a background of calcification, and the like can be confirmed, for example, as compared to a two-dimensional image (composite 2D image) generated through a technology such as MinIP. Further, the two-dimensional image data generated by the image generation function 22 is not also affected by artifacts associated with movement of an X-ray tube in tomosynthesis imaging.

According to the third embodiment described above, since the image acquisition function 21 which acquires a plurality of pieces of projection data acquired through tomosynthesis imaging of the test object and some projection data in which angles associated with two-dimensional image data are about 0° from among the plurality of pieces of projection data as the first medical image data, and the image generation function 22 which generates the second medical image data of the same test object by inputting the first medical image data to the trained model 32 which generates the second medical image data that is two-dimensional image data associated with X-ray imaging on the basis of the first medical image data are provided, it is possible to obtain a high-definition two-dimensional image from images associated with tomosynthesis imaging.

Furthermore, according to the third embodiment, since the image acquisition function 21 which acquires volume data reconstructed from the plurality of pieces of projection data acquired through tomosynthesis imaging of the test object and some tomographic image data in which angles associated with two-dimensional image data are about 0° from among tomographic image data of the volume data as the first medical image data, and the image generation function 22 which generates the second medical image data of the same test object by inputting the first medical image data to the trained model 32 which generates the second medical image data that is two-dimensional image data associated with X-ray imaging on the basis of the first medical image data are provided, it is possible to obtain a high-definition two-dimensional image from images associated with tomosynthesis imaging.

Specific Example of Third Embodiment

Figure 10:
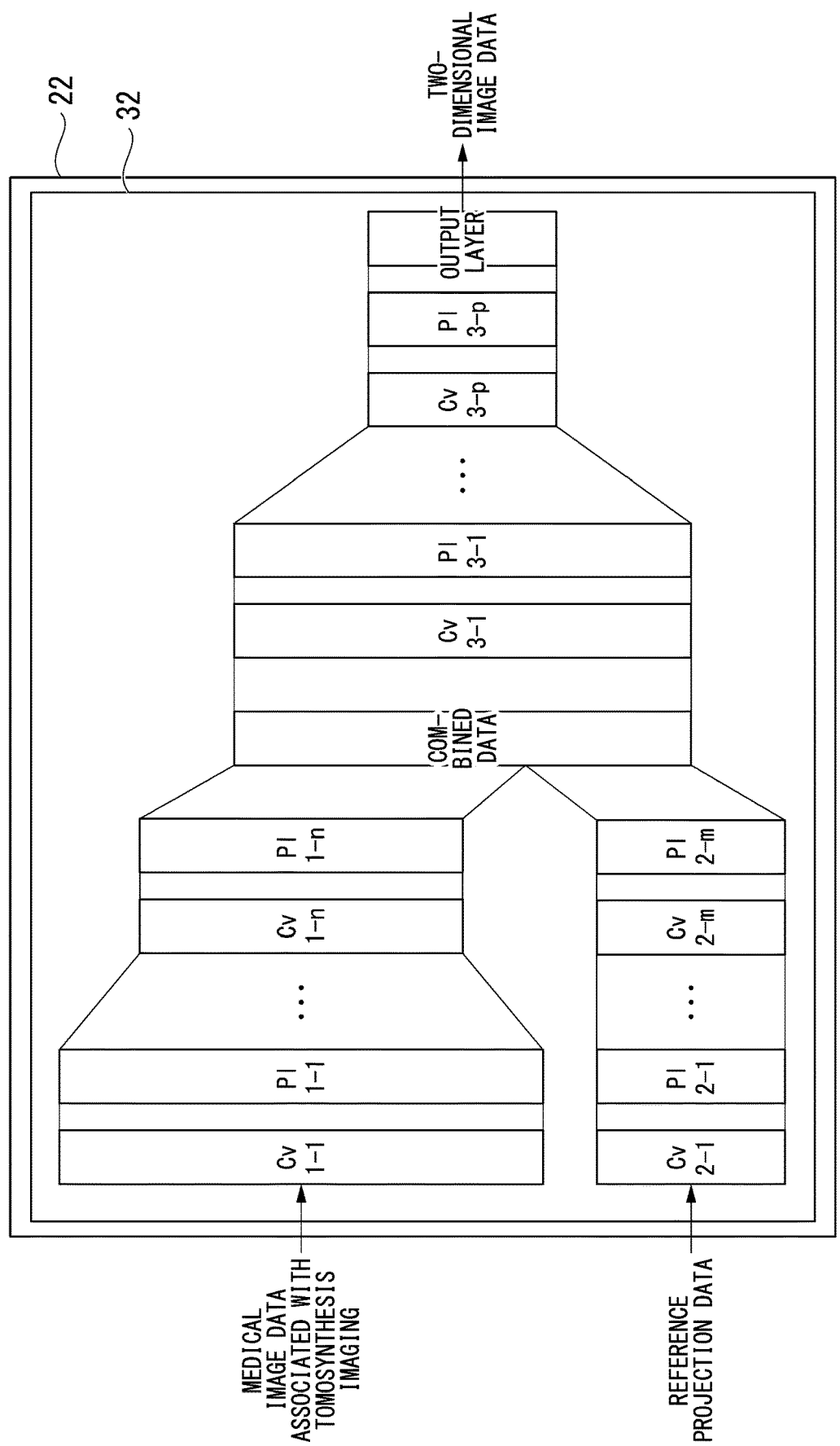
FIG. 10 is a diagram showing a more detailed example of a data flow during operation of the image generation function 22 according to the third embodiment.

The trained model 32 in the third embodiment may be generated in the following form, for example. FIG. 10 is a diagram showing an example of details of the trained model 32 in the third embodiment. The trained model 32 is a network using a CNN. As shown, the trained model 32 may be generated through deep learning which obtains parameters of a CNN having a convolution layer and a pooling layer using back propagation, for example. An activation function such as ReLU may be interposed between the convolution layer and the pooling layer. The trained model 32 may separate a CNN applied to medical image data associated with tomosynthesis imaging of a test object from a CNN applied to reference projection data in an input layer, for example. The reference projection data is some projection data in which angles associated with two-dimensional image data are about 0° from among a plurality of pieces of projection data acquired through tomosynthesis imaging of the test object or some tomographic image data in which angles associated with two-dimensional image data are about 0° from among tomographic image data of volume data reconstructed from a plurality of pieces of projection data acquired through tomosynthesis imaging of the test object. In addition, learning is performed such that, in any layer (a layer from which features have been extracted to a certain degree) to an output layer, outputs of CNNs are combined (concatenate) and combined data is further input to the CNNs to obtain two-dimensional image data. In the figure, it is assumed that the CNN applied to medical image data associated with tomosynthesis imaging of a test object is composed of n layers and the CNN applied to the reference projection data is composed of m layers. The numbers n and m of layers may be the same value or different values. Further, a CNN may not be applied to the reference projection data and the reference projection data may be combined with a middle layer of the CNN on the side of the medical image data associated with tomosynthesis imaging of the test object. Although the dimension decreases with a decreasing distance to the output layer in a general CNN, processing may be advanced while maintaining the same dimension by appropriately adding an outer frame part through extrapolation in the embodiment.

Fourth Embodiment

Figure 11:
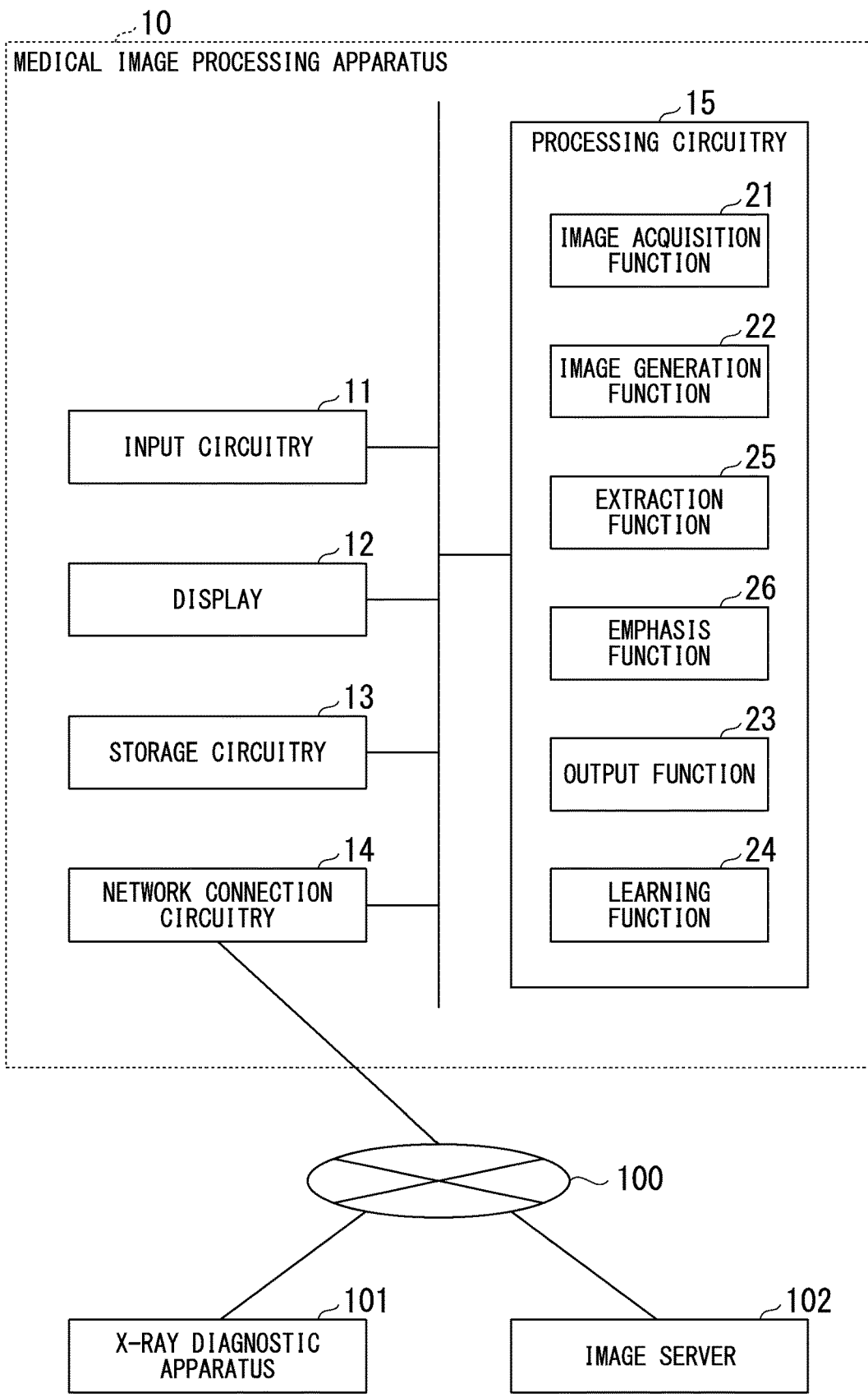
FIG. 11 is a block diagram showing an example of a configuration of a medical image processing apparatus 10 according to a fourth embodiment.

Hereinafter, a fourth embodiment will be described. FIG. 11 is a block diagram showing an example of a configuration of a medical image processing apparatus 10 according to the fourth embodiment. The medical image processing apparatus 10 includes input circuitry 11, a display 12, storage circuitry 13, network connection circuitry 14, and processing circuitry 15. Components other than the processing circuitry 15 are the same as those described in the first to third embodiments.

As shown in FIG. 11, the processing circuitry 15 according to the fourth embodiment realizes an image acquisition function 21, an image generation function 22, an output function 23, a learning function 24, an extraction function 25, and an emphasis function 26. These functions are stored in the storage circuitry 13 in the form of programs. The image acquisition function 21 and the image generation function 22 function after the trained model 32 has been generated and the output function 23 and the learning function 24 function to generate the trained model 32. The extraction function 25 and the emphasis function 26 function when two-dimensional image data is generated using the trained model 32.

The image acquisition function 21, the image generation function 22, the output function 23 and the learning function 24 have the same configurations and functions as those in any of the first to third embodiments. That is, the first medical image data and the trained model may be the same as those in any of the first to third embodiments. Accordingly, description of processing during learning is omitted.

Figure 12:
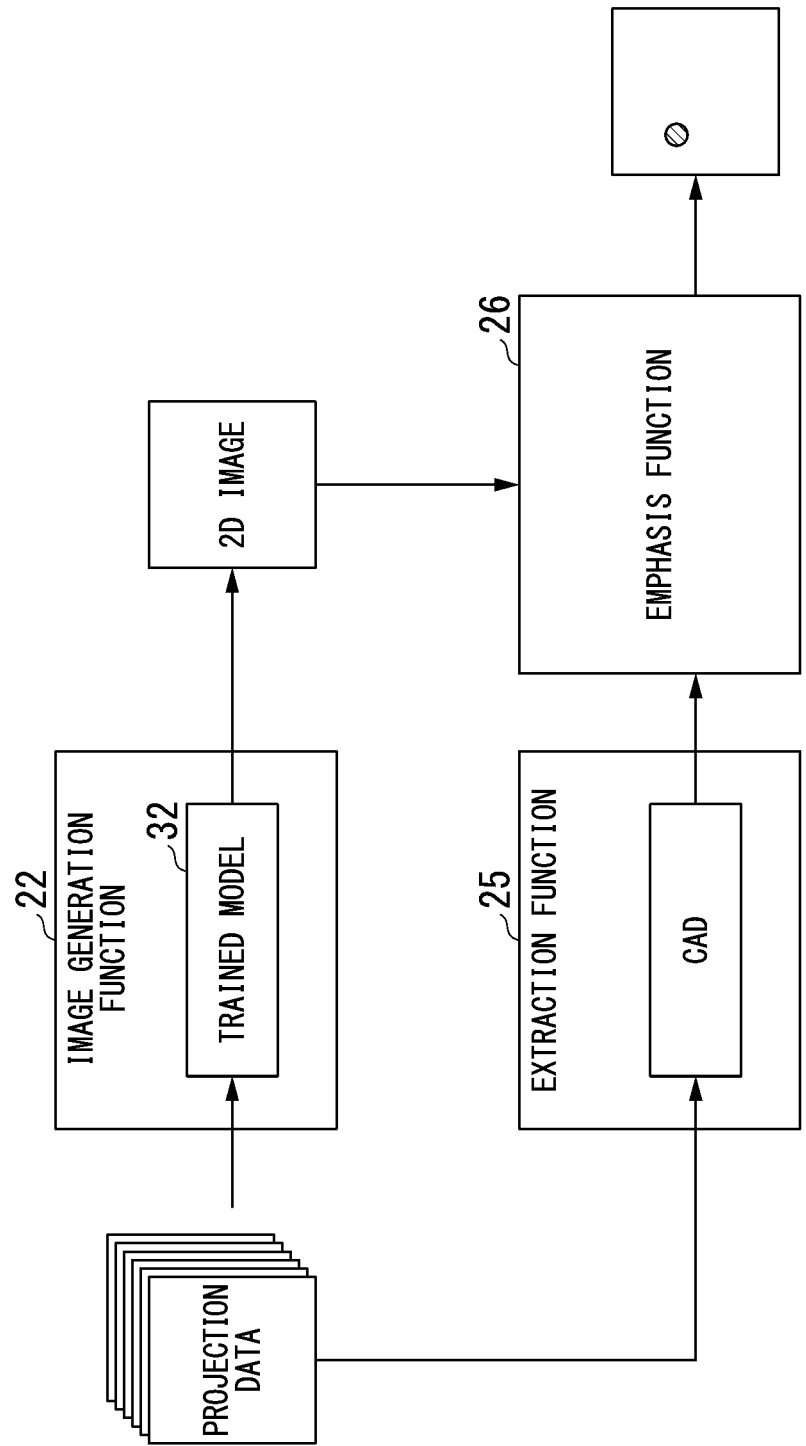
FIG. 12 is a diagram showing an example of a data flow during operation of an image generation function 22 according to the fourth embodiment.

As shown in FIG. 12, during operation, the extraction function 25 performs image processing on a plurality of pieces of projection data (first medical image data) acquired through tomosynthesis imaging of a test object, extracts the position of a lesion candidate in images and identifies the lesion type. In image processing of the extraction function 25, any method such as machine learning, morphological operation, or edge extraction may be used. Further, the extraction function 25 may perform image processing on volume data (first medical image data) reconstructed from a plurality of pieces of projection data acquired through tomosynthesis imaging of the test object, extract the position of a lesion candidate in images and identify the lesion type. The emphasis function 26 performs image processing for causing the position of the lesion candidate extracted by the extraction function 25 to be recognizable on two-dimensional image data generated by inputting the plurality of pieces of projection data acquired through tomosynthesis imaging of the test object to the trained model 32 through the image generation function 22 and causes the display 12 to display the processed images. Image processing performed by the emphasis function 26 is processing of adding an effect image that emphasizes the position of a lesion candidate to an image or adding information (including annotation such as letters and figures) representing a lesion type. By performing such processing, it is possible to cause the display 12 to display two-dimensional image data in a form easier to understand. According to the fourth embodiment described above, since the extraction function 25 and the emphasis function 26 are further provided, it is possible to cause the display 12 to display two-dimensional image data in a form easier to understand.

Fifth Embodiment

Hereinafter, a fifth embodiment will be described. A medical image processing apparatus 10 of the fifth embodiment has the same configuration as that of the medical image processing apparatus 10 of the fourth embodiment. However, the medical image processing apparatus 10 of the fifth embodiment may or may not include the emphasis function 26. In addition, in the fifth embodiment, the first medical image data and the trained model may be the same as those in any of the first to third embodiments. Accordingly, description of processing during learning is omitted.

Figure 13:
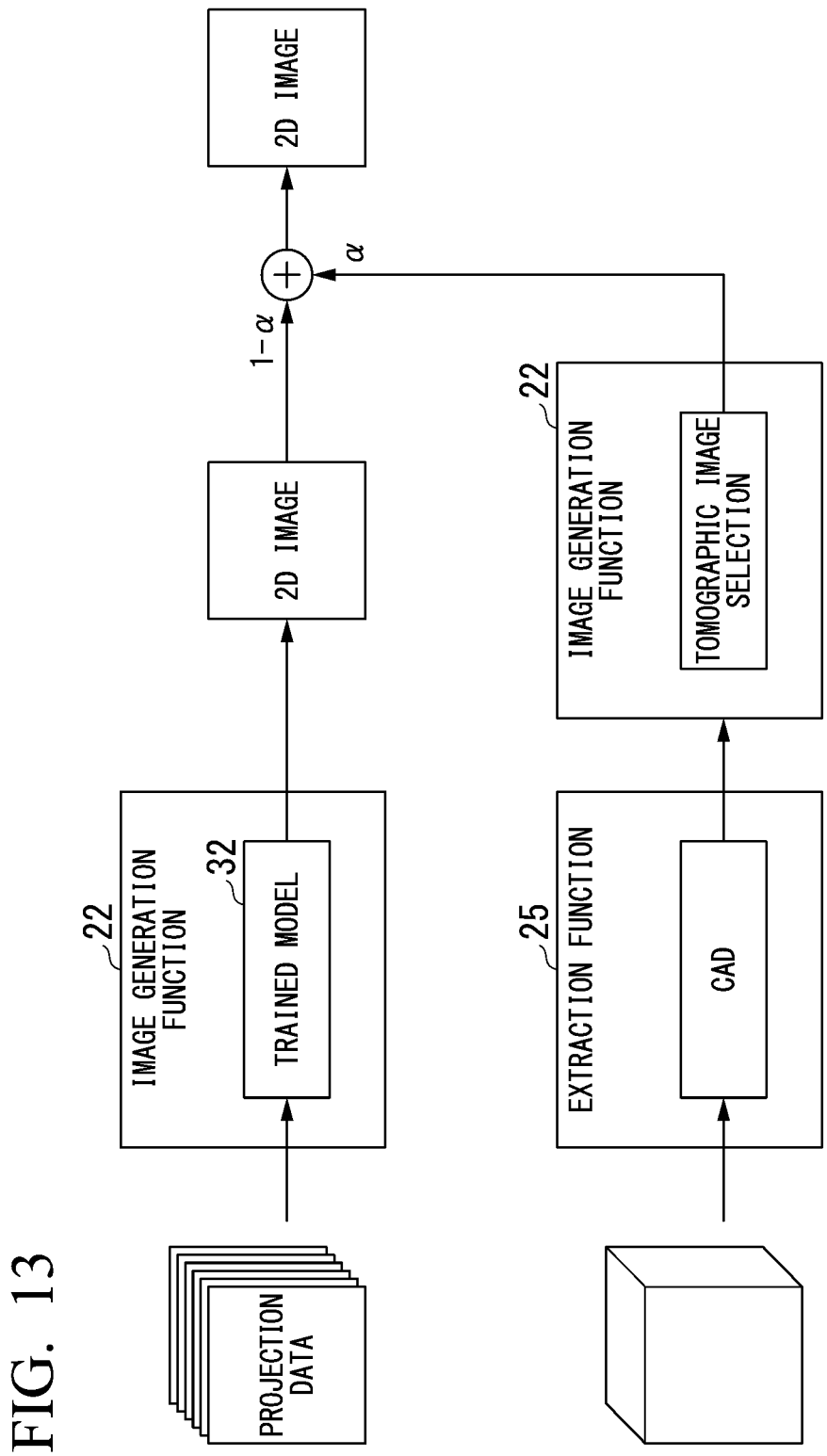
FIG. 13 is a diagram showing an example of a data flow during operation of an image generation function 22 according to a fifth embodiment.

As shown in FIG. 13, the image generation function 22 according to the fifth embodiment blends any tomographic image data of volume data reconstructed from a plurality of pieces of projection data acquired through tomosynthesis imaging in two-dimensional image data output from the trained model 32 at a predetermined blend ratio to generate two-dimensional image data when an output image is generated. Any tomographic image data is tomographic image data including the position of a lesion candidate extracted by the extraction function 25, for example. When the position of the lesion candidate has a certain degree of size, tomographic image data that penetrates the center of the range of the position of the lesion candidate may be selected as any tomographic image data, for example. Furthermore, the present invention is not limited thereto and tomographic image data selected by a user may be selected or tomographic image data that penetrates the centers of volume data may be selected uniformly.

The image generation function 22 adds image data obtained by multiplying tomographic image data including the position of a lesion candidate extracted by the extraction function 25 by $\alpha$ to image data obtained by multiplying two-dimensional image data output from the trained model 32 by $1-\alpha$ to generate blended two-dimensional image data. $\alpha$ is a coefficient in the range of 0 to 1.

According to the fifth embodiment described above, it is possible to improve visibility of an internal state of a test object P by blending tomographic images of volume data reconstructed form a plurality of pieces of projection data acquired through tomosynthesis imaging.

Sixth Embodiment

Hereinafter, a sixth embodiment will be described. In the sixth embodiment, processing during learning and processing during operation are performed for mini batch regions obtained by dividing, in a slice plane, a plurality of pieces of projection data acquired through tomosynthesis imaging of a test object or volume data reconstructed from the plurality of pieces of projection data, and some projection data in which angles associated with two-dimensional image data are about 0° from among the plurality of pieces of projection data or some tomographic image data in which angles associated with two-dimensional image data are about 0°, which is extracted from the volume data.

Figure 14:
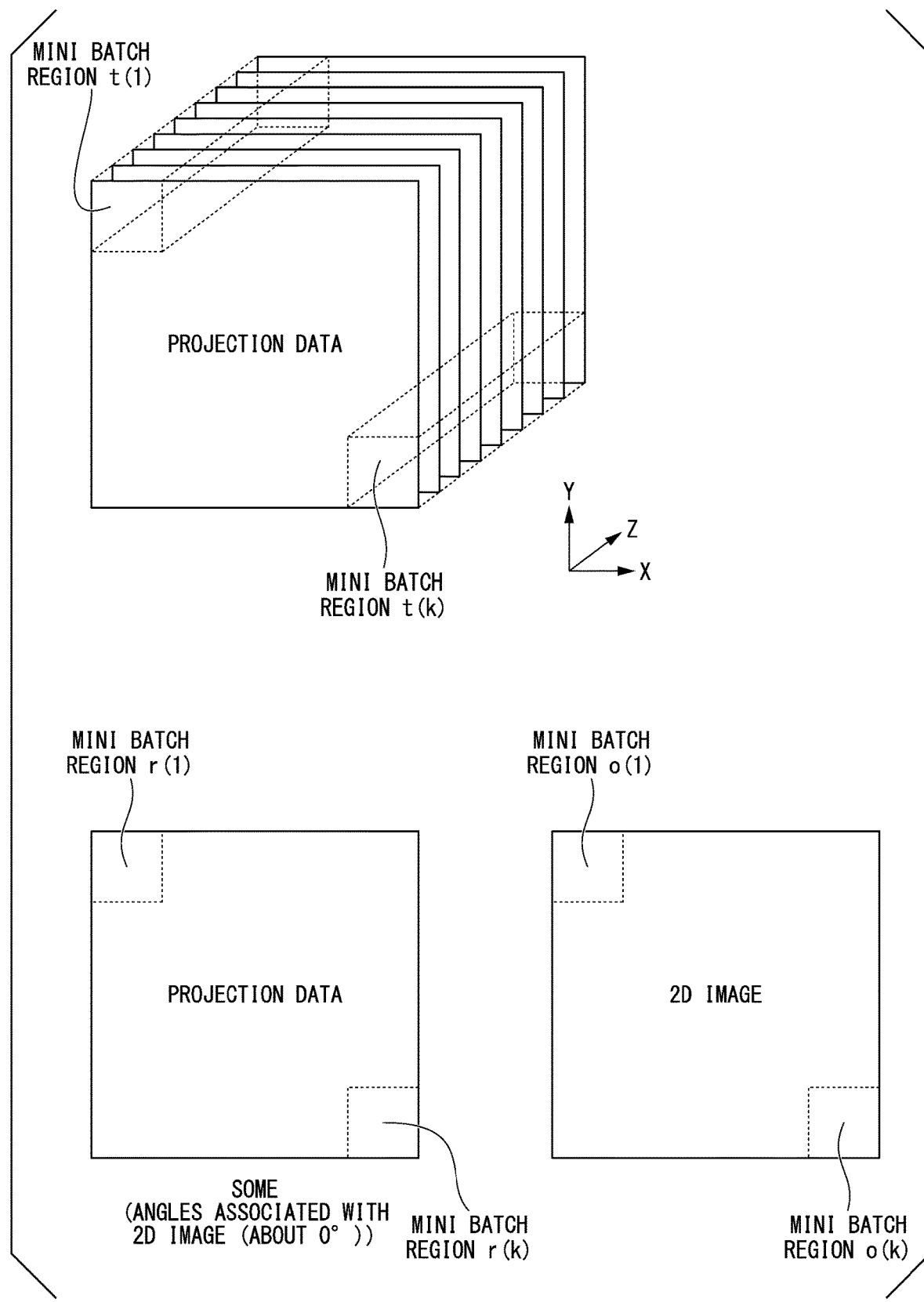
FIG. 14 is a diagram for describing a mini batch region.

As shown in FIG. 14, an output function 23 in the sixth embodiment performs processing of cutting out data associated with k mini batch regions with respect to a plurality of pieces of projection data acquired through tomosynthesis imaging of a test object and some projection data in which angles associated with two-dimensional image data are about 0° from among the plurality of pieces of projection data in order to generate training input data. k is a natural number. Instead of this, the output function 23 may perform processing of cutting out the data associated with the k mini batch regions with respect to volume data reconstructed from the plurality of pieces of projection data and some tomographic image data in which angles associated with two-dimensional image data are about 0°, which is extracted from the volume data. Mini batch regions t(1) to t(k) are spatial regions obtained by dividing the plurality of pieces of projection data in the slice plane such that they include all of information in a direction perpendicular to the slice direction. In addition, mini batch regions r(1) to r(k) are regions at positions in the slice plane which correspond to the mini batch regions t(1) to t(k). Further, the output function 23 also performs processing of cutting out data associated with mini batch regions o(1) to o(k) with respect to two-dimensional image data associated with X-ray imaging of the same test object in the same manner in order to generate training output data. The mini batch regions o(1) to o(k) are regions at positions in the slice plane which correspond to the mini batch regions t(1) to t(k).

Figure 15:
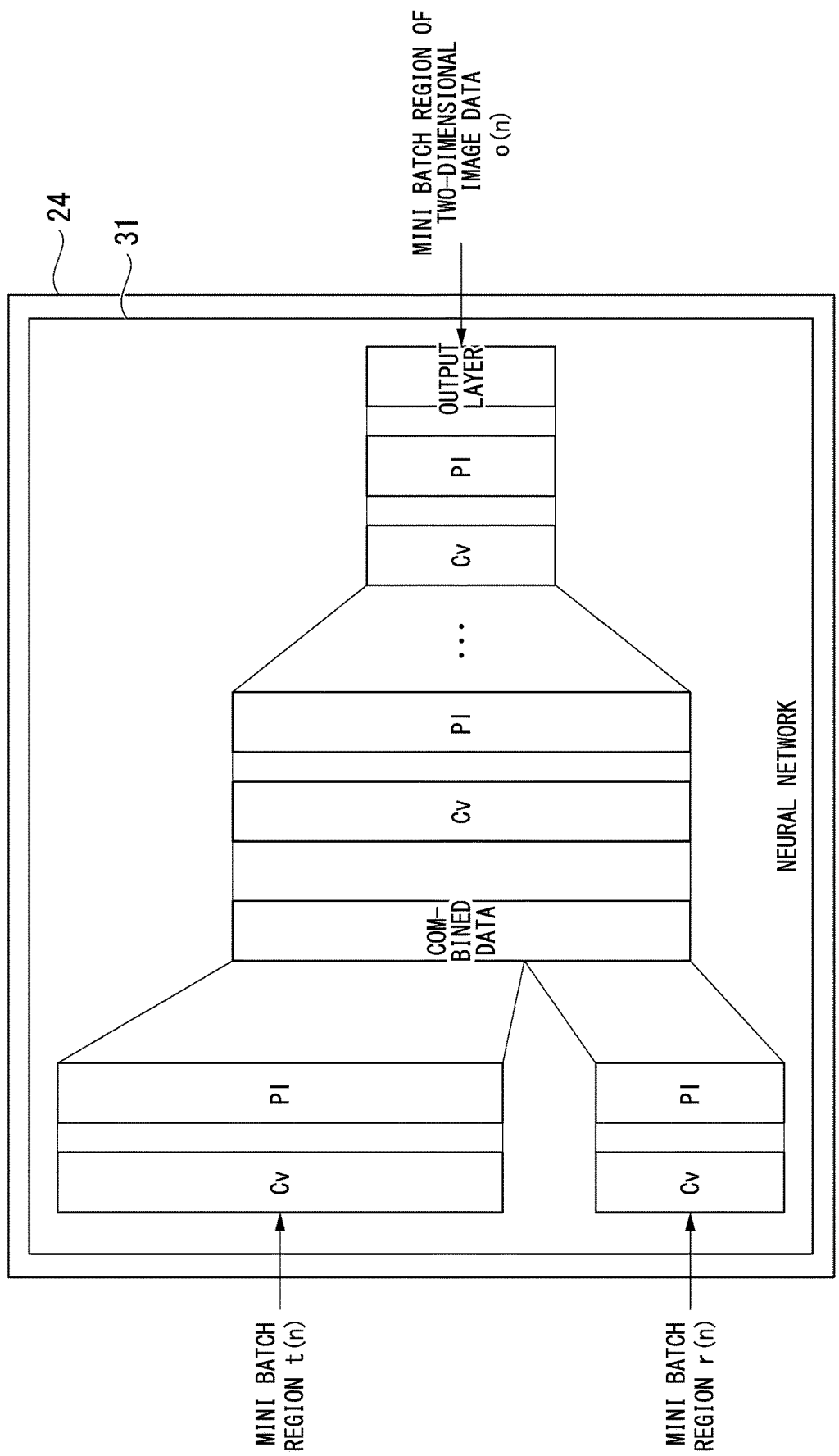
FIG. 15 is a diagram showing an example of a data flow during learning of a learning function 24 according to a sixth embodiment.

A learning function 24 according to the sixth embodiment performs learning processing with respect to respective mini batch regions. As shown in FIG. 15, a neural network 31 in the sixth embodiment is a model in which an input layer is divided into a part to which a mini batch region t(n) in the plurality of pieces of projection data acquired through tomosynthesis imaging of the test object is input and a part to which a mini batch region r(n) in some projection data in which angles associated with two-dimensional image data are about 0° from among the plurality of pieces of projection data is input, and thus information is separately propagated to an arbitrary layer. In the figure, n is 1 to k and is an identifier of a mini batch region. The neural network 31 is configured such that information propagated from both directions is combined in an arbitrary layer and then information is propagated through full combination, for example, from the combined data. The learning function 24 performs update of parameter data of the neural network 31 such that a result of processing of training input data (data of the mini batch region t(n) and the mini batch region r(n)) in the neural network 31 approaches training output data (data of the mini batch region o(n)), known as learning, whenever a data set for learning is input. The parameter data of the neural network 31 is adjusted and updated through a method such as back propagation of a CNN, for example. The learning function 24 determines that learning ends when a change rate of the parameter data converges within a threshold value. The learning function 24 generates a trained model 32 having a form of a deep neural network (DNN), for example, on the basis of the parameter data after learning. The trained model 32 is stored in the storage circuitry 13 and read from the storage circuitry 13 during operation. Further, the trained model 32 may be constructed using an integrated circuit such as an ASIC or an FPGA.

The operation of the medical image processing apparatus 10 configured as above during operation will be described below.

Figure 16:
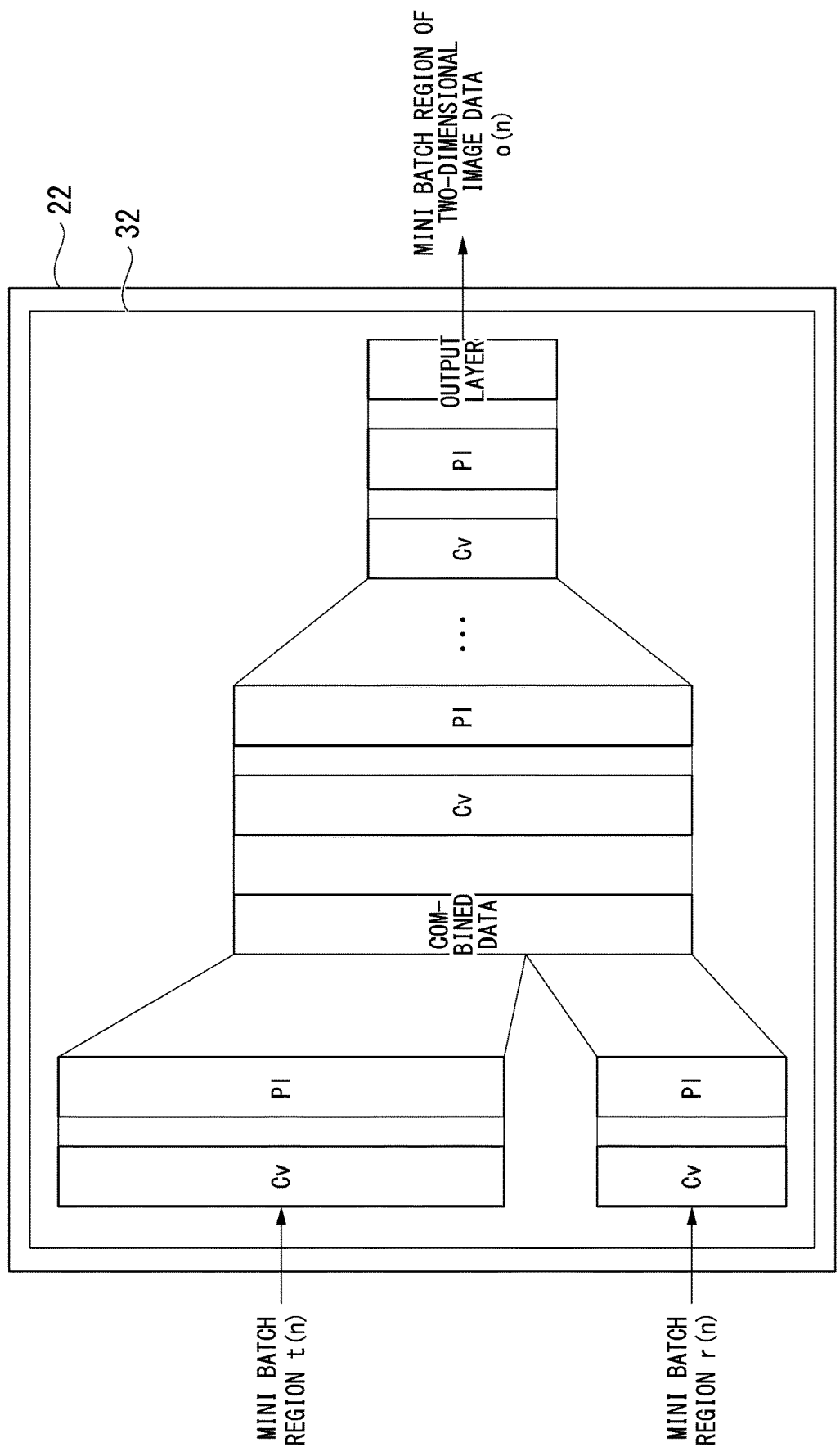
FIG. 16 is a diagram showing an example of a data flow during operation of an image generation function 22 according to the sixth embodiment.

As shown in FIG. 16, the image generation function 22 generates part of the mini batch region o(n) of two-dimensional image data of a test object by inputting data of the mini batch region t(n) in a plurality of pieces of projection data acquired through tomosynthesis imaging of the test object and data of the mini batch region r(n) in some projection data in which angles associated with two-dimensional image data are about 0° from among the plurality of pieces of projection data to the trained model 32.

According to the sixth embodiment described above, it is possible to increase the number of pieces of learning data and reduce processing load of a processor in addition to achievement of the same effects as those of the first to third embodiments.

In addition, according to the sixth embodiment, it is possible to prevent a characteristic portion in an image from being concealed in a relationship with surrounding regions.

Seventh Embodiment

Hereinafter, a seventh embodiment will be described. The seventh embodiment relates to an X-ray diagnostic apparatus equipped with the medical image processing apparatuses of the above-described first to sixth embodiments. In the following, an example in which an X-ray diagnostic apparatus is equipped with the medical image processing apparatus 1 of the first embodiment will be representatively described.

Figure 17:
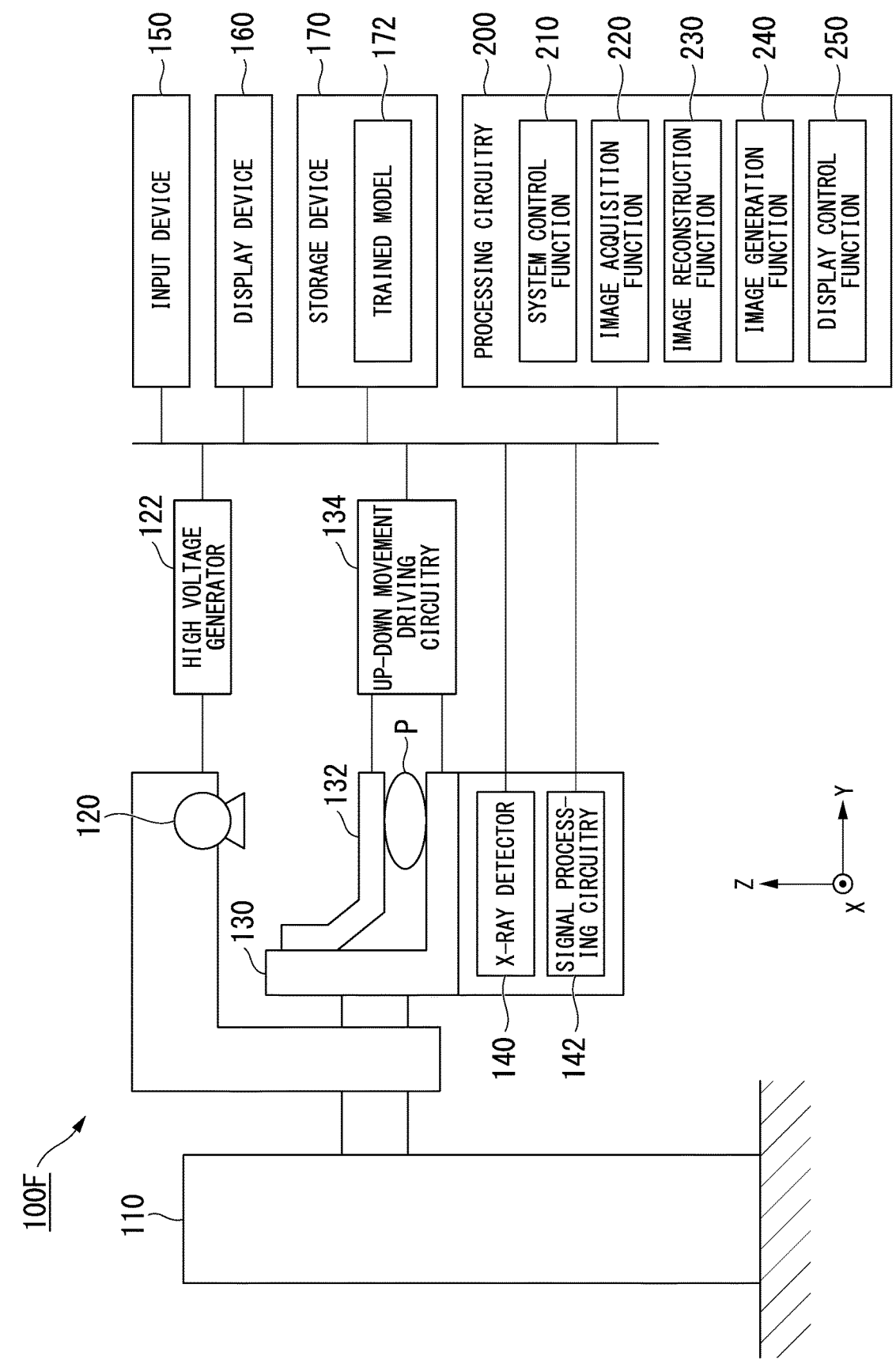
FIG. 17 is a diagram showing an example of a configuration of an X-ray diagnostic apparatus 100F according to a seventh embodiment.

FIG. 17 is a diagram showing an example of a configuration of an X-ray diagnostic apparatus 100F including medical image processing according to the seventh embodiment. For example, the X-ray diagnostic apparatus 100F may include a stand 110, an X-ray tube 120, a high voltage generator 122, an imaging stand 130, a pressing plate 132, up-down movement driving circuitry 134, an X-ray detector 140, signal processing circuitry 142, an input device 150, a display device 160, and processing circuitry 200.

The stand 110 supports the imaging stand 130, the pressing plate 132, the X-ray detector 140, and the signal processing circuitry 142 such that they can move in the vertical direction (Z direction in the figure).

The X-ray tube 120 generates X-rays using a high voltage supplied from the high voltage generator 122. The X-ray generated by the X-ray tube 120 is radiated to the position (radiation target position) of the breast of a test object P. The X-ray tube 120 can move to draw an arc around the Y axis in the figure such that a radiation angle for the radiation target position can be changed. The high voltage generator 122 is connected to the X-ray tube 120 and supplies a high voltage for generating X-rays to the X-ray tube 120 according to control of the processing circuitry 200.

The imaging stand 130 is a stand supporting the breast of the test object P. The imaging stand 130 has a supporting surface on which the breast of the test object P is placed. The pressing plate 132 is attached to the upper part of the imaging stand 130 (in the +Z direction in the figure) to face the supporting surface of the imaging stand 130. The pressing plate 132 can move in a direction (Z direction in the figure) in which it becomes far away from or approaches the imaging stand 130 while remaining in a state in which it faces the supporting surface of the imaging stand 130.

The breast of the test object P is placed between the imaging stand 130 and the pressing plate 132. Accordingly, the breast of the test object P is pressed when the pressing plate 132 moves in a direction in which it approaches the imaging stand 130. Therefore, it is possible to obtain a clearer image by thinly stretching and extending the breast of the test object P to reduce overlap of mammary gland.

The up-down movement driving circuitry 134 is connected to the imaging stand 130 and moves the imaging stand 130 up and down according to control of the processing circuitry 200. In addition, the up-down movement driving circuitry 134 is connected to the pressing plate 132 and moves the pressing plate 132 up and down according to control of the processing circuitry 200.

The X-ray diagnostic apparatus 100F can generate a mammographic image such as a mediolateral-oblique (MLO) image or a cranio-caudal (CC) image on the basis of projection data collected by fixing the positions of the imaging stand 130 and the pressing plate 132 in an MLO direction or a CC direction and radiating X-rays in a state a specific radiation angle to the breast of the test object P is maintained.

The X-ray detector 140 is a flat panel detector (FPD), for example. The X-ray detector 140 detects X-rays that have passed through the test object P and converts the X-rays into an electronic signal. The X-ray detector 140 has thin film transistor (TFT) sensor pixels, for example. The X-ray detector 140 stores the electronic signal that is a detection result therein. The signal processing circuitry 142 reads the electronic signal converted by the X-ray detector 140, generates projection data on the basis of the electronic signal and stores the projection data in storage circuitry 170.

The input device 150 receives an input operation of an operator operating the X-ray diagnostic apparatus 100F. For example, the input device 150 includes a mouse, a keyboard, buttons, a trackball, a joystick, a touch panel, or the like. The input device 150 converts details of the input operation into electronic signals and outputs the electronic signals to the processing circuitry 200.

The display device 160 display various images generated by the processing circuitry 200. The various images include a graphical user interface (GUI) images for receiving a touch operation of the operator, cross-sectional images generated from tomosynthesis, two-dimensional images, etc.

The storage circuitry 170 includes storage circuitry having a non-transitory storage medium such as an HDD, a flash memory or a ROM, and storage circuitry such as a RAM or a register, for example. The storage circuitry 170 stores projection data, tomosynthesis, a program executed by the two-dimensional image processing circuitry 200, a trained model 172, etc. In addition, the trained model 172 may be described in such a manner that it is embedded in a program.

The processing circuitry 200 includes a system control function 210, an image acquisition function 220, an image reconstruction function 230, an image generation function 240, and a display control function 250, for example. The processing circuitry 200 realizes these functions by a hardware processor executing programs stored in the storage circuitry 170, for example. The hardware processor has been described above.

The system control function 210 controls the entire X-ray diagnostic apparatus 100F. For example, the system control function 210 may generate control signals with respect to the high voltage generator 122, the up-down movement driving circuitry 134, the X-ray detector 140 and the like and outputs the control signals thereto.

Figure 18:
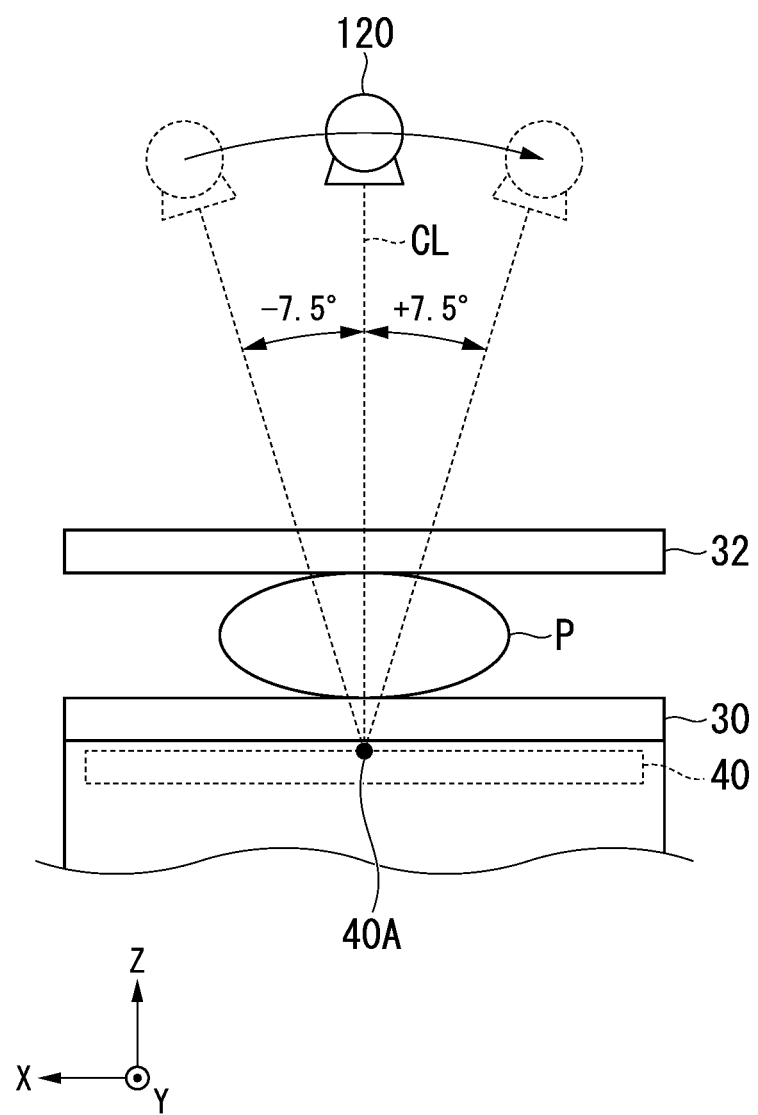
FIG. 18 is a diagram showing an example of a projection data acquisition method performed by an X-ray diagnostic apparatus 100F.

An example of details of control performed by the system control function 210 will be described. FIG. 18 is a diagram showing an example of operation of tomosynthesis imaging performed by the X-ray diagnostic apparatus 100E For example, in an imaging step, the X-ray tube 120 is driven by a driving mechanism which is not shown to move while drawing an arc within a range of −7.5° to +7.5° with a position (neutral position) on a normal line CL with respect to a detection surface of the X-ray detector 140, which passes through a center point 40A in the X direction of the detection surface, as a center. The above-described "angles are 0°" represents that the X-ray tube 120 is at the neutral position. In this process, the X-ray detector 140 and the signal processing circuitry 142 generate 17 pieces of projection data such that angle widths with respect to the center point 40A of the x-ray tube 120 are uniform. These 17 pieces of projection data include projection data generated when the X-ray tube 120 is on the normal line CL. According to this operation, a plurality of pieces of projection data for tomosynthesis can be acquired.

The image acquisition function 220 reads various images from the storage circuitry 170 and provides the read images to other functions. For example, the image acquisition function 220 performs logarithmic conversion processing, offset correction processing, sensitivity correction processing, beam hardening correction processing on projection data stored in the storage circuitry 170 through the signal processing circuitry 142 and provides the corrected projection data to other functions.

The image reconstruction function 230 performs reconstruction processing on the corrected projection data on which correction processing has been performed by the image acquisition function 220 to generate tomosynthesis. For example, the image reconstruction function 230 generates tomosynthesis by performing image back projection processing based on reverse radon transformation on a plurality of pieces of projection data. As a specific example of image back projection processing, a filtered back projection method, a successive approximation method (expected value maximization), a shift addition method, and the like are known, and the X-ray diagnostic apparatus 100F can employ any method with respect to these specific methods.

The image generation function 240 generates a two-dimensional image by inputting medical image data associated with tomosynthesis imaging of the test object to the trained model 172.

The display control function 250 generates an image signal for causing the display device 160 to display the two-dimensional image generated by the image generation function 240 and the like and outputs the image signal to the display device 160.

According to the seventh embodiment described above, it is possible to cause the X-ray diagnostic apparatus to operate as any medical image processing apparatus of the first to sixth embodiments.

OTHERS

Although the mammography apparatus has been exemplified as the X-ray diagnostic apparatus in the above-described embodiments, a two-dimensional image (an image corresponding to an X-ray image acquired through X-ray imaging of 0°) may be generated from data obtained through tomosynthesis imaging performed in an X-ray TV apparatus when the X-ray diagnostic apparatus is applied to the X-ray TV apparatus. The above-described embodiments can be represented as a medical image processing apparatus including: a storage device which stores a program; and a hardware processor, wherein the hardware processor is configured, by executing the program, to acquire medical image data associated with tomosynthesis imaging of a test object as first medical image data and to generate second medical image data of the test object by inputting the first medical image data to a trained model which generates the second medical image data that is two-dimensional image data on the basis of the first medical image data.

According to at least one of the above-described embodiments, since the image acquirer 21 which acquires medical image data associated with tomosynthesis imaging of a test object as first medical image data and the image generator 22 which generates second medical image data of the test object by inputting the first medical image data to the trained model 32 which generates the second medical image data that is two-dimensional image data on the basis of the first medical image data are provided, it is possible to generate a two-dimensional image with higher visibility.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus comprising:
processing circuitry configured to
acquire medical image data on the basis of tomosynthesis imaging of a breast of a test object, and
input the acquired medical image data of the test object to a trained model to acquire mammography image data of the test object, the trained model being generated by learning of mammography image data on the basis of mammography imaging of a breast of a person and image data on the basis of tomosynthesis imaging of the breast of the person who is subjected to the mammography imaging,
wherein
the processing circuitry is further configured to
extract, from the medical image data acquired through the tomosynthesis imaging, projection data or reconstructed data of the projection data, an angle of which corresponds to an angle of the mammography imaging of the test object, and
input both the extracted projection data or reconstructed data and the acquired medical image data to the trained model to acquire the mammography image data of the test object.

2. The medical image processing apparatus according to claim 1, wherein
the processing circuitry is further configured to
extract a region of interest included in the acquired medical image data on the basis of the tomosynthesis imaging, and
emphasize a region associated with the extracted region of interest in the acquired mammography image data.

3. The medical image processing apparatus according to claim 2, wherein
the processing circuitry is configured to extract a lesion on the basis of a result of computer aided detection (CAD) as the region of interest.

4. The medical image processing apparatus according to claim 1, wherein
the processing circuitry is further configured to blend tomographic image data included in the medical image data on the basis of the tomosynthesis imaging with the mammography image data of the test object at a predetermined ratio to generate image data.

5. A learning method comprising:
generating a trained model which generates mammography image data from medical image data on the basis of tomosynthesis imaging of a breast of a test object, using a data set including a pair of mammography medical image data on the basis of mammography imaging of a breast of a person and medical image data on the basis of the tomosynthesis imaging of the breast of the person who is subjected to the mammography imaging,
wherein
outputting the mammography image data of the test object from the trained model when both projection data or reconstructed data of the projection data and the medical image data are input, the projection data or reconstructed data being extracted from the medical image data acquired through the tomosynthesis imaging are input, an angle of the projection data or reconstructed data corresponding to an angle of the mammography imaging of the test object.

6. An X-ray diagnostic apparatus comprising:
an imager configured to perform tomosynthesis imaging on a test object by radiating the test object with X-rays at a plurality of angles; and
a medical image processing apparatus according to claim 1.

7. A medical image processing method, using a computer, comprising:
acquiring medical image data on the basis of tomosynthesis imaging of a breast of a test object, and
inputting the medical image data of the test object to a trained model to acquire mammography image data of the test object, the trained model being generated by learning of mammography image data on the basis of mammography imaging of a breast of a person and image data on the basis of tomosynthesis imaging of the breast of the person who is subjected to the mammography imaging,
wherein
the medical image processing method further comprises
extracting, from the medical image data acquired through the tomosynthesis imaging, projection data or reconstructed data of the projection data, an angle of which corresponds to an angle of the mammography imaging of the test object, and
inputting both the extracted projection data or reconstructed data and the acquired medical image data to the trained model to acquire the mammography image data of the test object.

* * * * *